US008488902B2

(12) United States Patent
Bertram (10) Patent No.: US 8,488,902 B2
(45) Date of Patent: Jul. 16, 2013

(54) DETECTION VALUES CORRECTION APPARATUS

(75) Inventor: Matthias Bertram, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 697 days.

(21) Appl. No.: 12/692,786

(22) Filed: Jan. 25, 2010

(65) Prior Publication Data
US 2010/0189376 A1     Jul. 29, 2010

(30) Foreign Application Priority Data
Jan. 29, 2009   (EP) .................................... 09151598

(51) Int. Cl.
*G06K 9/40*   (2006.01)
(52) U.S. Cl.
USPC .......................................................... 382/274
(58) Field of Classification Search
USPC .... 250/363.04; 378/4, 5, 7, 21, 901; 382/131, 382/274, 275
See application file for complete search history.

(56) References Cited

U.S. PATENT DOCUMENTS

| | | | | |
|---|---|---|---|---|
| 4,323,977 A * | 4/1982 | Arseneau | ....................... | 382/275 |
| 4,850,002 A * | 7/1989 | Harding et al. | .................. | 378/87 |
| 5,666,391 A | 9/1997 | Ohnesorge et al. | | |
| 7,136,450 B2 | 11/2006 | Ying et al. | | |
| 7,473,900 B2 * | 1/2009 | Vija | .......................... | 250/363.04 |
| 2005/0127302 A1 * | 6/2005 | Kojima et al. | ............ | 250/363.03 |
| 2005/0276373 A1 * | 12/2005 | Ying et al. | ......................... | 378/7 |
| 2007/0104313 A1 * | 5/2007 | Tesic et al. | ....................... | 378/37 |
| 2008/0075347 A1 | 3/2008 | Ruhrnschopf | | |

FOREIGN PATENT DOCUMENTS

| | | |
|---|---|---|
| EP | 1363121 A1 | 11/2003 |
| WO | 2007148263 A1 | 12/2007 |

OTHER PUBLICATIONS

Ohnesorge, B., et al.; Efficient object scatter correction algorithm for third and fourth generation CT scanners; 1999; Eur. Radiol.; 9:563-569.

* cited by examiner

*Primary Examiner* — Gregory F Cunningham (57) ABSTRACT

The present invention relates to a detection values correction apparatus for correcting detection values of a projection image of a multi-energy imaging system. A scatter contribution providing unit provides scatter contributions for different intensities, different energies and different locations on the detection surface of the detection values. A scatter contributions combining unit combines scatter contributions for correcting a detection value, wherein the combined scatter contributions represent the contribution of the scatter, which is caused by radiation of the other detection values of the projection image, to the detection value to be corrected and wherein the scatter contributions are combined under consideration of the intensity, energy and location on the detection surface of the other detection values. A correction unit scatter corrects the detection value of the projection image by using the combined scatter contributions.

20 Claims, 3 Drawing Sheets

DETECTION VALUES CORRECTION APPARATUS

CROSS REFERENCE TO RELATED APPLICATIONS

This application claims the benefit of EPO provisional application serial no. 09151598.1 filed Jan. 29, 2009, which is incorporated herein by reference.

FIELD OF THE INVENTION

The present invention relates to a detection values correction apparatus, a scatter contribution providing unit and a multi-energy imaging system. The invention relates further to a detection values correction method, a scatter contribution providing method, a multi-energy imaging method and corresponding computer programs.

BACKGROUND OF THE INVENTION

WO 2007/148263 A1 discloses a method for generating a set of kernels for convolution error compensation of a projection image of a physical object recorded by an imaging system like a computed tomography system. The set of kernels is calculated in such a way that for each pixel of the projection image an asymmetric scatter distribution for error compensation is calculated representing an X-ray scatter originating along a ray from an X-ray source to the pixel. The projection image is scatter corrected by performing a convolution error compensation using the generated set of kernels. If several projection images belonging to different angular positions of the radiation source are scatter corrected and if these scatter corrected projection image are used for reconstructing an image of the object, artifacts caused by scatter are reduced in the reconstructed image, thereby improving the quality of the reconstructed image.

But, if the set of kernels is used to perform convolution error compensation on detection values of a multi-energy computed tomography system, an image reconstructed by using the corrected detection values still comprises scatter artifacts caused by the spectral dependency of the scattering process.

SUMMARY OF THE INVENTION

It is an object of the present invention to provide a detection values correction apparatus and a detection values correction method for correcting detection values of a projection image of a multi-energy imaging system, wherein the corrected detection values, in particular, an image reconstructed by using the corrected detection values, comprise fewer artifacts caused by scattering. It is a further object of the present invention to provide a corresponding scatter contribution providing unit, a scatter contribution providing method, a multi-energy imaging system and a multi-energy imaging method. Moreover, it is an object of the present invention to provide corresponding computer programs for controlling the detection values correction apparatus, the scatter contribution providing unit and the multi-energy imaging system in accordance with the detection values correction method, the scatter contribution providing method and the multi-energy imaging method, respectively.

In an aspect of the present invention a detection values correction apparatus for correcting detection values of a projection image of a multi-energy imaging system comprising a radiation source for emitting radiation for traversing an object and a detection unit comprising a detection surface for generating the detection values depending on the radiation after having traversed the object, wherein a detection value represents an intensity, an energy and a location on the detection surface, wherein the detection values correction apparatus comprises:

- a scatter contribution providing unit for providing scatter contributions for different intensities, different energies and different locations on the detection surface of the detection values, wherein a scatter contribution represents the contribution of the scatter, which is generated by radiation of a detection value representing an intensity, an energy and a location on the detection surface, to the detection value to be corrected,
- a scatter contributions combining unit for combining scatter contributions for correcting a detection value, wherein the combined scatter contributions represent the contribution of the scatter, which is caused by radiation of the other detection values of the projection image, to the detection value to be corrected and wherein the scatter contributions are combined under consideration of the intensity, energy and location on the detection surface of the other detection values,
- a correction unit for scatter correcting the detection value of the projection image by using the combined scatter contributions.

Since for correcting a detection value combined scatter contributions are used, wherein the combined scatter contributions represent the contribution of the scatter, which is caused by radiation of the other detection values of the projection image, to the detection value to be corrected and wherein the scatter contributions are combined under consideration of the intensity, energy and location on the detection surface of the other detection values, the scatter contributions to a detection value can be considered energy dependent. This allows considering the spectral dependence of the scattering process while correcting the detection values for scattering, thereby allowing correcting the detection values of a multi-energy imaging system such that the corrected detection values, in particular, an image reconstructed by using these correction detection values, comprises fewer artifacts caused by scattering.

The multi-energy imaging system is preferentially an imaging system that generates detection values which correspond to at least one of different spectra of the radiation incident on the object and an energy-window of the detection unit, thereby generating spectral detection values. The multi-energy imaging system is preferentially an imaging system which acquires detection values forming a projection image like a C-arm system or a computed tomography system.

It is preferred that the energy represented by a detection value is preferentially an energy spectrum defined by at least one of a spectrum of the radiation incident on the object and an energy-window, which can also be regarded as an energy bin, of the detection unit. Thus, a detection value preferentially represents an energy spectrum, an intensity and a location of the detection surface, i.e a detection value defines preferentially an intensity measured for an energy spectrum of radiation, which has met the detection surface at the respective location. If the radiation source can have different positions with respect to the object, the detection value preferentially further represents a radiation source position, i.e. a detection value defines preferentially an intensity measured for an energy spectrum of radiation, which has met the detection surface at the respective location, while the radiation source was located at the respective position.

The projection image is preferentially an image formed by the detection values on the detection surface.

The scatter contribution providing unit provides scatter contributions for different intensities, different energies and different locations on the detection surface of the detection values, i.e. the scatter contribution to a value to be corrected depends on the intensity, the energy and the location on the detection surface of another detection value, wherein, in particular, the energy of the detection value to be corrected and of the other detection value are the same. The scatter contribution represents the contribution of the scatter, which is generated by radiation of a detection value representing intensity, energy and location on the detection surface, to the detection value to be corrected, i.e. the radiation that caused a detection value not being the detection value, which is actually to be corrected, and that is named "other detection value", generates scatter while traveling through the object, wherein this scatter depends on the intensity and location on the detection surface of the other detection value, which has preferentially the same energy as the detection value to be corrected, and wherein the part of this scatter that falls onto the location on the detection surface, at which the detection value to be corrected is located, is the scatter contribution "of the other detection value" to the detection value to be corrected.

The scatter contributions combining unit combines scatter contributions for correcting a detection value, wherein the combined scatter contributions represent the contribution of the scatter, which is caused by radiation of the other detection values of the projection image, to the detection value to be corrected and wherein the scatter contributions are combined under consideration of the intensity, energy and location on the detection surface of the other detection values, i.e. depending on the intensity, the energy and the location on the detection surface of the other detection values scatter contributions to the detection value to be corrected are selected and these selected scatter contributions are combined. In particular, for correcting a detection value only scatter contributions are combined, which correspond to the same energy as the energy of the detection value to be corrected. The combination is preferentially a weighted or unweighted summation of the scatter contributions.

It is further preferred that the scatter contribution providing unit is adapted to provide scatter images, wherein each scatter image represents scatter contributions to the detection values of the projection image generated by radiation of a detection value representing an intensity, an energy and a location on the detection surface. Thus, a scatter image represents the scatter, which is generated along a path of radiation to a detection value representing an intensity, an energy and a location on the detection surface and which is detected on the detection surface by the detection unit, i.e. the scatter image can be regarded as a representation of a projection image caused by scatter, which is detected, if the radiation travels through the object only to a single detector element which detects the detection value representing an intensity, an energy and location on the detection surface.

It is preferred that the scatter contributions providing unit is adapted to provide a scatter image by simulating and/or measuring a scatter generated by radiation along a path to a detection value representing an intensity, an energy and a location on the detection surface through a model of the object. In an embodiment, the scatter images only represent the respective scatter. In another embodiment, the scatter images represent scatter divided by primary radiation which will be described in more detail further below.

The model can be any model that allows estimating the scatter caused by radiation traveling through the object. The model has, for example, a spherical or elliptical shape. Moreover, the model can have the shape of a slab. Preferentially, the dimensions and/or the shape of the model depend on the respective detection value which has to be scatter corrected. Thus, preferentially for different possible detection values different dimensions and/or shapes of the model are used for simulating and/or measuring a scatter image, thereby generating different scatter images that depend on possible values of the detection values.

The model can be, for example, a water model. However, it is preferred that the model of the object is a model representing at least one of a) multiple materials and b) an average material comprising a scatter characteristic being an average of scatter characteristics of multiple materials. The multiple materials are preferentially water, bone and optionally a contrast agent. The model representing an average material is preferentially a model representing a homogenous average material that comprises scatter characteristics that have been determined by averaging the scattering characteristics of different materials of a model comprising multiple materials. For example, a model comprising water, bone and optionally a contrast agent can be replaced by a model comprising a homogenous average material, wherein the average material is determined such that the scattering characteristics of the average material are the average of the scattering characteristics of the water, bone and optionally a contrast agent. The use of a model representing at least one multiple materials and an average material, for example, instead of a water model, allows to determine the scatter images more realistic, because the object through which the radiation traverses comprises generally not only water, but multiple materials. This further reduces the scatter artifacts in the detection values, in particular, in images being reconstructed by using the corrected detection values.

A detection value is assigned to a path of the radiation causing the respective detection value. The scatter image representing the scatter caused if radiation runs along this path, does not have to be determined by simulating or measuring the scatter if the radiation travels along exactly this path. As estimation, the scatter, which is caused if the radiation runs along a path being perpendicular to a detection surface of the detection unit and meeting the detection surface at the location at which the respective detection value has been acquired, can be simulated or measured for determining the scatter image representing the scatter produced by radiation running along a path originating at the radiation source position and meeting the detection surface at the location at which the respective detection value has been acquired.

The scatter contribution providing unit is preferentially adapted to provide scatter images depending on the intensity of the detection values. Since the scatter caused by radiation traversing the object depends—inter alias—on the intensity of the detection values, by providing scatter images, which depend on the intensity of the detection values, scatter images which correspond to the intensity of the detection values can be used for correcting the detection values.

For correcting a detection value of a view preferentially the scatter, i.e. the corresponding scatter contributions, produced by the radiation along the paths of the other detection values of the same view are used for correcting the respective detection value. This is preferentially performed by a convolution-like procedure, wherein the scatter images can be regarded as a kernel for convoluting the detection values of a view, thereby determining the combined scatter contribution of the respective detection value. This convolution-like procedure that uses the scatter image as a kernel will be described further below in more detail with reference to equations (4) and (6).

It is further preferred that the scatter contribution providing unit is adapted to provide scatter images being parameterized. In particular, the scatter images are represented as parameterized functions. The functions can, for example, be determined by firstly generating complete scatter images and then by parameterizing these complete scatter images, in order to reduce the number of scatter images which might be stored in a storing unit of the scatter contribution providing unit and which have to be accessed. Instead of storing and accessing a lot of scatter images, only a few parameters can be stored and accessed. For example, a polynomial function of degree n, in particular, of degree 2 can be fitted to the respective scatter image, wherein only the parameters of the polynomial function have to be stored and accessed and not the complete respective scatter image. Furthermore, if the scatter images are symmetrically, a Gaussian function can be fitted to the respective scatter image, wherein a scatter image is preferentially described by the parameters width and peak intensity in two directions, if the scatter image is a two-dimensional image.

It is further preferred that the detection values correction apparatus is adapted to correct detection values of a projection image of a multi-energy imaging system being a multi-energy computed tomography system, wherein the detection value correction apparatus further comprises a reconstruction unit for reconstructing an image of the object from the corrected detection values. This allows reconstructing computed tomography images of the object having fewer artifacts caused by scattering.

In a further aspect of the present invention a scatter contribution providing unit for providing scatter contributions being usable with a detection values correction apparatus for correcting detection values of a projection image of a multi-energy imaging system comprising a radiation source for emitting radiation for traversing an object and a detection unit comprising a detection surface for generating the detection values depending on the radiation after having traversed the object is presented, wherein a detection value represents an intensity, an energy and a location on the detection surface, wherein the scatter contribution providing unit is adapted to provide scatter contributions for different intensities, different energies and different locations on the detection surface of the detection values, wherein a scatter contribution represents the contribution of the scatter, which is generated by radiation of a detection value representing an intensity, an energy and a location on the detection surface, to the detection value to be corrected.

The scatter contribution providing unit can be a unit that is adapted to generate scatter contributions, in particular, scatter images, for example, as described above.

In a further aspect of the present invention a multi-energy imaging system is provided,
wherein the multi-energy imaging system comprises:
a radiation source for emitting radiation for traversing an object,
a detection unit comprising a detection surface for generating detection values of a projection image depending on the radiation after having traversed the object, wherein a detection value represents an intensity, an energy and a location on the detection surface,
a detection correction apparatus as defined in claim 1.

It is preferred that the radiation source and the detection unit are adapted to acquire detection values representing predefined energies, wherein the scatter contribution providing unit is adapted to store predetermined scatter contributions for different intensities, the predefined energies and different locations on the detection surface of the detection values.

Thus, a set of predetermined scatter contributions can be provided being adapted to the actual multi-energy imaging system, i.e. scatter contributions are predetermined that correspond to possible intensities, energies and locations on the detection surface represented by detection values of the multi-energy imaging system.

It is further preferred that the radiation source and the detection unit are adapted to acquire detection values representing predefined energies, wherein the scatter contribution providing unit is adapted to provide the scatter contributions by combining predetermined scatter contributions, which have been predetermined for different intensities, different energies and different locations on the detection surface, such that the resulting scatter contributions represent the contribution of the scatter, which is caused by radiation of detection values representing different intensities, the predefined energies and different locations on the detection surface, to a detection value to be corrected. Thus, a set of predetermined scatter contributions, in particular, of scatter images, can be provided wherein these predetermined scatter contributions are combined to correspond to possible energies of detection values of the actual multi-imaging system, i.e. a set of predetermined scatter contributions can be provided which can be used with different multi-energy imaging systems. The combination can be performed by interpolation, for example, by a weighted cumulation of the relevant scatter contributions.

In a further aspect of the present invention a detection values correction method for correcting detection values of a projection image of a multi-energy imaging system comprising a radiation source for emitting radiation for traversing an object and a detection unit comprising a detection surface for generating the detection values depending on the radiation after having traversed the object is presented, wherein a detection value represents an intensity, an energy and a location on the detection surface, wherein the detection values correction method comprises following steps:

providing scatter contributions for different intensities, different energies and different locations on the detection surface of the detection values, wherein a scatter contribution represents the contribution of the scatter, which is generated by radiation of a detection value representing an intensity, an energy and a location on the detection surface, to the detection value to be corrected, combining scatter contributions for correcting a detection value, wherein the combined scatter contributions represent the contribution of the scatter, which is caused by radiation of the other detection values of the projection image, to the detection value to be corrected and wherein the scatter contributions are combined under consideration of the intensity, energy and location on the detection surface of the other detection values, scatter correcting the detection value of the projection image by using the combined scatter contributions.

The detection values can be present in different energy views, wherein the detection values of an energy view are detection values of a projection image representing the same energy. The scatter correction can be performed for each energy view resulting in several scatter corrected energy views.

The steps of combining scatter contributions and scatter correcting can be performed iteratively, wherein after an iteration step the scatter corrected detection values of an energy view are used for combining scatter contributions and scatter correcting in the next iteration step.

In a further aspect of the present invention a scatter contribution providing method for providing scatter contributions being usable with a detection values correction method for correcting detection values of a projection image of a multi-energy imaging system comprising a radiation source for emitting radiation for traversing an object and a detection unit comprising a detection surface for generating the detection values depending on the radiation after having traversed the object is presented, wherein a detection value represents an intensity, an energy and a location on the detection surface, wherein scatter contributions for different intensities, different energies and different locations on the detection surface of the detection values are provided, wherein a scatter contribution represents the contribution of the scatter, which is caused by radiation of a detection value representing an intensity, an energy and a location on the detection surface, to the detection value to be corrected.

In a further aspect of the present invention a multi-energy imaging method is provided, wherein the multi-energy computed tomography method comprises following steps:

emitting radiation for traversing an object by a radiation source, generating detection values of a projection image depending on the radiation after having traversed the object, wherein a detection value represents an intensity, an energy and a location on the detection surface, by a detection unit comprising a detection surface, correcting the detection values of the projection image by the detection values correction method as defined in claim 10.

In a further aspect of the present invention a computer program for correcting detection values of a projection image of a multi-energy imaging system comprising a radiation source for emitting radiation for traversing an object and a detection unit comprising a detection surface for generating the detection values depending on the radiation after having traversed the object is presented, wherein a detection value represents an intensity, an energy and a location on the detection surface, the computer program comprising program code means for causing a detection values correction apparatus as defined in claim 1 to carry out the steps of the detection values correction method as defined in claim 10, when the computer program is run on a computer controlling the detection values correction apparatus.

In a further aspect of the present invention a computer program for providing scatter contributions being usable with a detection values correction method for correcting detection values of a projection image of a multi-energy imaging system comprising a radiation source for emitting radiation for traversing an object and a detection unit comprising a detection surface for generating the detection values depending on the radiation after having traversed the object is presented, wherein a detection value represents an intensity, an energy and a location on the detection surface, the computer program comprising program code means for causing a scatter contribution providing unit as defined in claim 6 to carry out the steps of the scatter contribution providing method as defined in claim 11, when the computer program is run on a computer controlling the scatter contribution providing unit.

In a further aspect of the present invention a computer program for controlling a multi-energy imaging system is presented, the computer program comprising program code means for causing a multi-energy imaging system as defined in claim 7 to carry out the steps of the multi-energy imaging method as defined in claim 12, when the computer program is run on a computer controlling the multi-energy imaging system.

It shall be understood that the detection values correction apparatus of claim 1, the scatter contribution providing unit of claim 6, the multi-energy computed tomography system of claim 7, the detection values correction method of claim 10, the scatter contribution providing unit of claim 11, the multi-energy computed tomography method of claim 12 and the computer programs of claims 13 to 15 have similar and/or identical preferred embodiments as defined in the dependent claims.

It shall be understood that a preferred embodiment of the invention can also be any combination of the dependent claims with the respective independent claim.

BRIEF DESCRIPTION OF THE DRAWINGS

These and other aspects of the invention will be apparent from and elucidated with reference to the embodiments described hereinafter. In the following drawings

DETAILED DESCRIPTION OF EMBODIMENTS

Figure 1:
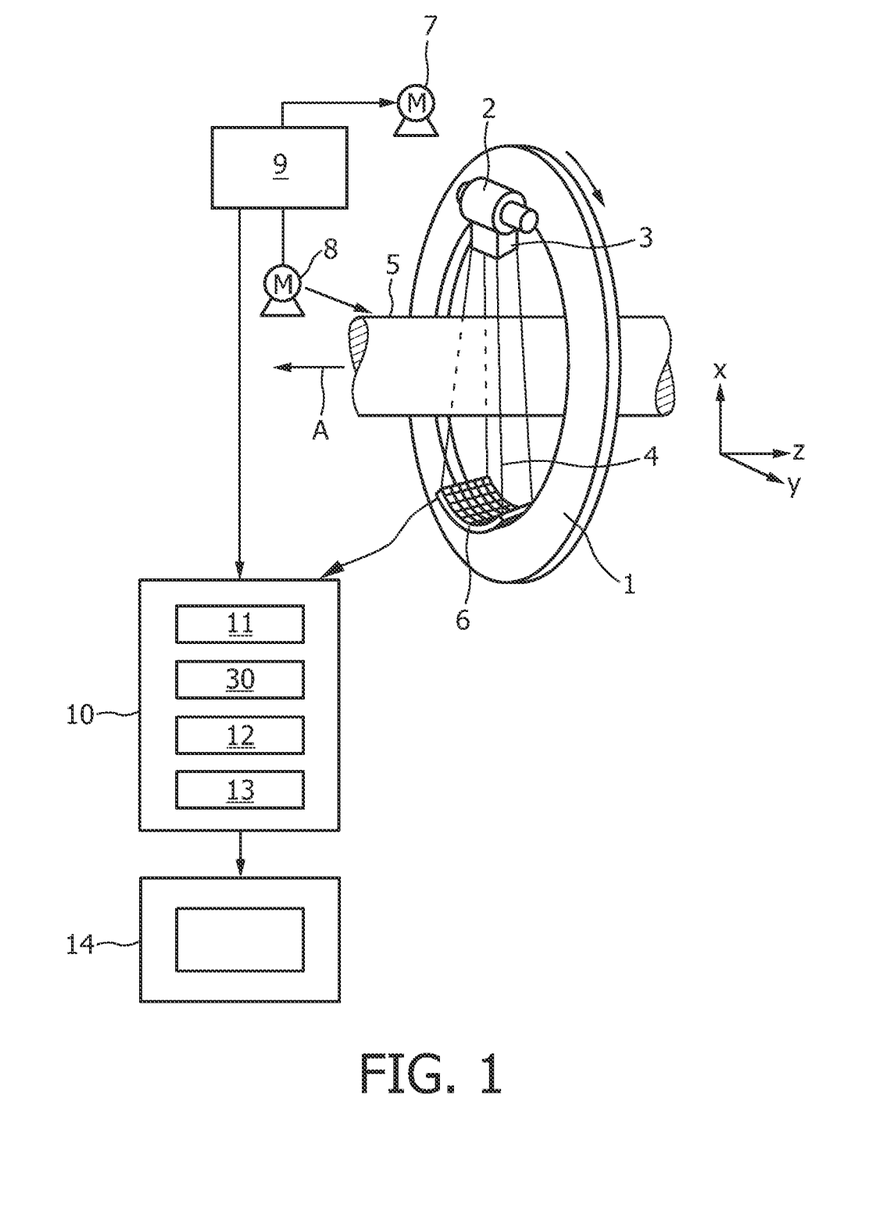
FIG. 1 shows schematically and exemplarily an embodiment of a multi-energy computed tomography system.

FIG. 1 shows schematically and exemplarily a multi-energy computed tomography system for imaging a region of interest. The multi-energy computed tomography system includes a gantry 1 which is capable of rotation around a rotational axis A which extends parallel to the z-direction. A radiation source 2 being an X-ray tube is mounted on the gantry 1. The radiation source 2 is provided with a collimator 3, which forms, in this embodiment, a conical radiation beam 4 from the radiation generated by the radiation source 2. The radiation traverses an object (not shown), such as a patient, located in an examination zone 5, which is, in this embodiment, cylindrical. After having traversed the examination zone the radiation beam 4 is incident on a detection unit 6 that comprises a two-dimensional detection surface. The detection unit 6 is mounted on the gantry 1.

The multi-energy computed tomography system is adapted to provide different spectra of radiation incident on the examination zone, in particular, incident on the object. Furthermore, the detection unit 6 is adapted to provide different energy-windows in which radiation which has traversed the examination zone, in particular, which have traversed the object, can be detected. Thus, the multi-energy computed tomography system is adapted to acquire detection values belonging to different energy spectra, i.e. belonging to different spectra of the radiation source and/or to different energy-windows of the detection unit, wherein each detection value represents an intensity, an energy spectrum, a location on the detection surface and a position of the radiation source relative to the object. The location on the detection surface and the position of the radiation source relative to the object define the path of the radiation which belongs to the detection value. This means, preferentially each detection value depends on the spectrum of radiation incident on the object and/or the energy of the radiation after having traversed the object. Moreover, each detection value depends on the intensity of the radiation after having traversed the object, and the corresponding path of radiation.

The multi-energy computed tomography system comprises two motors 7, 8. The gantry 1 is driven at a preferably constant but adjustable angular speed by the motor 7. The motor 8 is provided for displacing the object, for example, a patient, who is arranged on a patient table in the examination zone 5, parallel to the direction of the rotational axis A or the z-axis. These motors 7, 8 are controlled by a control unit 9, for instance, such that the radiation source 2 and the examination zone 5 and, thus, the object within the examination zone move relatively to each other along a helical trajectory. However, it is also possible that the object or the examination zone 5 is not moved, but that only the radiation source 2 is rotated, i.e. that the radiation source moves along a circular trajectory relative to the object or the examination zone 5. Furthermore, in another embodiment, the collimator 3 can be adapted for forming another beam shape, in particular a fan beam, and the detection unit 6 can comprise a detection surface, which is shaped corresponding to the other beam shape, in particular, to the fan beam.

During a relative movement of the radiation source and the examination zone 5 the detection unit 6 generates detection values depending on the radiation incident on the detection surface of the detection unit 6. The detection values are projection data forming projection images, wherein detection values corresponding to the same radiation source position with respect to the object are regarded as a projection and form a projection image or view. The detection values are provided to a detection values correction apparatus 10 for correcting the detection values. The detection values correction apparatus 10 comprises a scatter contribution providing unit 11 for providing scatter contributions for different intensities, different energies and different locations on the detection surface, and optionally different radiation source positions with respect to the object, of the detection values, wherein a scatter contribution represents the contribution of the scatter, which is generated by radiation of a detection value representing an intensity, an energy, a location on the detection surface and optionally a radiation source position with respect to the object, to the detection value to be corrected. The detection values correction apparatus further comprises a scatter contributions combining unit 30 for combining scatter contributions for correcting a detection value, wherein the combined scatter contributions represent the contribution of the scatter, which is caused by radiation of the other detection values of the projection image, to the detection value to be corrected and wherein the scatter contributions are combined under consideration of the intensity, energy, location on the detection surface, and optionally radiation source position with respect to the object, of the other detection values. The detection values correction apparatus further comprises a correction unit 12 for scatter correcting the detection value of the projection image by using the combined scatter contributions. Moreover, the detection values correction apparatus 10 comprises a reconstruction unit 13 for reconstructing an image of the object from the corrected detection values. Also the detection values correction apparatus 10 is preferentially controlled by the control unit 9.

The image generated by the reconstruction unit 13 is provided to a display unit 14 for displaying the generated image.

The scatter contribution providing unit 11 is adapted to provide scatter images, wherein a scatter image represents a scatter produced by radiation running along a path through the object for at least one of a spectrum of the radiation incident on the object and an energy-window of the detection unit 6. Thus, for a given path through the object and a given energy distribution defined by at least one of a spectrum incident on the object and an energy-window of the detection unit the scatter image represents the scatter produced under these given conditions. The scatter image further depends on the intensity of the detection value that corresponds to the radiation which has traveled along the respective path, the location on the detection surface of the detection value and optionally on the radiation source position with respect to the object for the respective path.

The scatter contribution providing unit 11 is adapted to provide the scatter image by simulating and/or measuring a scatter caused by radiation running along a path through a model of the object for at least one of a spectral radiation incident on the object and an energy-window of the detection unit.

Figure 2:
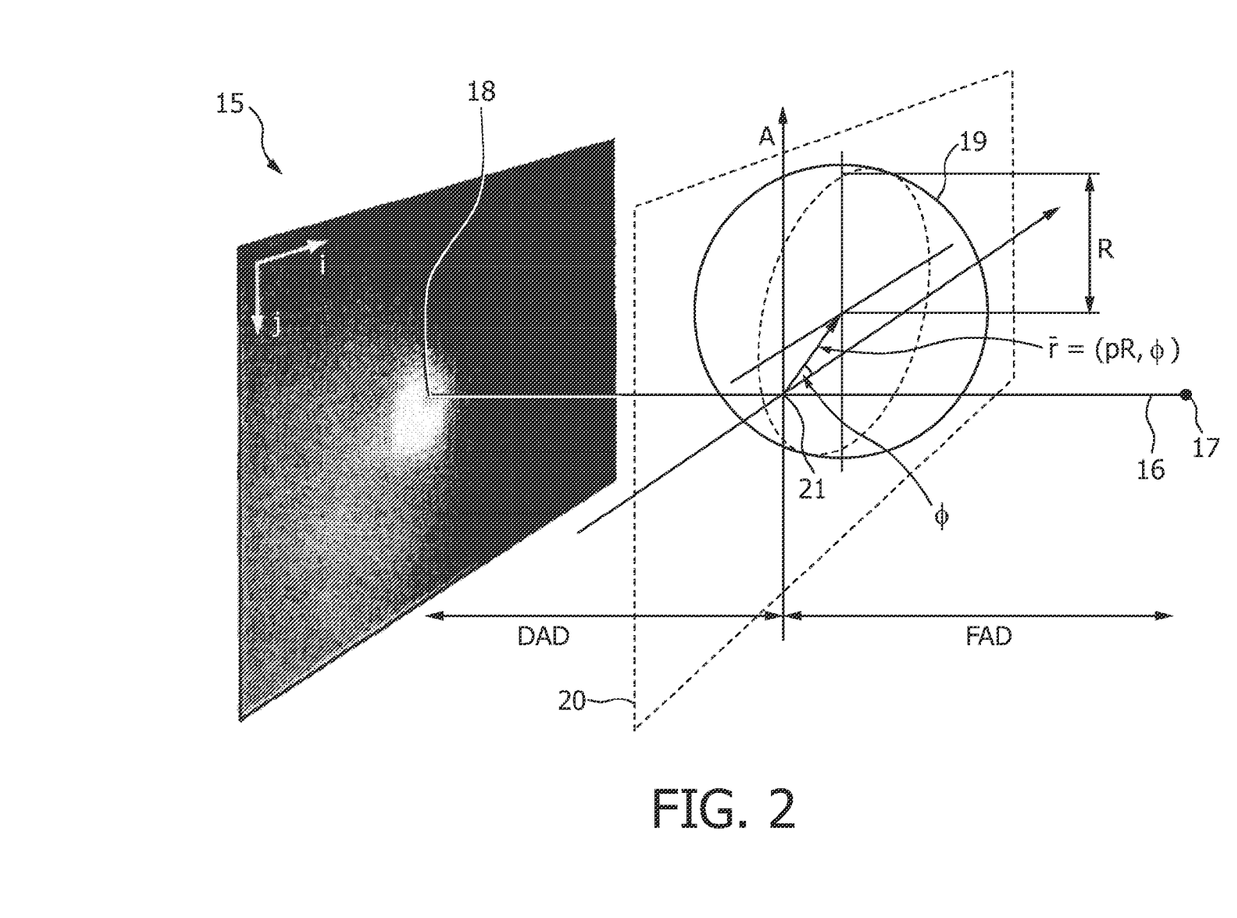
FIG. 2 shows schematically and exemplarily an arrangement for determining a scatter image.

A scatter image 15 is schematically and exemplarily shown in FIG. 2. The scatter image 15 shown in FIG. 2 is produced by a pencil beam 16 of radiation running from the focal spot 17 of a radiation source towards the two-dimensional detection surface of the detection unit, on which the scatter image is measured or simulated. The pencil beam 16 meets the two-dimensional detection surface at the position 18 defined by the variables i and j. The scatter represented by the scatter image 15 is caused by the pencil beam 16 traversing a model 19 of the object.

The model 19 is, in this embodiment, a sphere. However, in another embodiment instead of the sphere 19 another model can be used like, for example, an elliptical model or a slab model. It should be noted that the term "model of the object" does not refer to a substantially exact model of the object, which comprises, for example, the shape of the model. The model of the object can be any model that allows giving an estimation of the scatter during acquiring the detection values with a multi-energy imaging system. Furthermore, if a path of radiation belongs to a certain detection value, the scatter image representing the scatter produced while the radiation travels along this path does not have to be simulated and/or measured by using exactly the same path of radiation. As estimation, the scatter produced while traveling along a path of radiation being perpendicular to the detection surface and meeting the detection surface at the location at which the respective detection value has been acquired can be used for simulating and/or measuring the respective scatter image.

The sphere 19 resides in a plane 20 through the isocenter 21 parallel to the two-dimensional detector surface on which the scatter image 15 is located. In FIG. 2, FAD and DAD refer to the distance between the focal spot 17 and the rotational axis A and the distance between the two-dimensional detection surface and the rotational axis A, respectively. The sphere 19 has a radius R and has a positional shift with respect to the isocenter 21 within the plane 20 defined in polar coordinates by the vector $\vec{r}=(\rho R,\phi)$. The variable $\rho$ is the offset ratio and the variable $\phi$ is the offset angle. The scatter contribution providing unit is adapted to provide scatter images for different radius R, different positional shifts $\vec{r}$ and different locations at which the pencil beam meets the two-dimensional detection surface. Furthermore, the scatter contribution providing unit is adapted to provide these scatter images for different energy spectra, i.e. for several spectra incident on the model 19 and/or several energy-windows of the detection unit 6.

The model 19 of the object is comprised of water. In another embodiment, the model can be comprised of multiple materials which are, for example, water and bone. The model can further be comprised of a contrast agent. In a further embodiment, the model can be composed of a homogeneous average material. A preferred homogeneous average material is a hypothetic material which has an energy distribution dependent physical scatter cross section which is a weighted average of the energy distribution dependent physical scatter cross sections of other materials, such as water, bone, and contrast agent.

The detection values are assigned to a path of a radiation causing the respective detection value and are assigned to at least one of a spectrum of the radiation incident on the object and an energy-window of the detection unit 6. The detection values assigned to a path of the radiation originating at the same radiation source position form a view, which can also be regarded as a projection image. The detection values of a view assigned to the same energy, i.e. assigned to the same spectrum of radiation incident on the object and/or to the same energy-window of the detection unit 6, can be regarded as an energy view. For correcting the detection values of an energy view the scatter contribution combining unit 30 is adapted to combine scatter contributions, in particular, scatter images representing a scatter produced by radiation running along paths originating at the radiation source position of the respective energy view for the energy of the respective energy view. The correction unit 12 is adapted to correct the detection values of the energy view by using the respective combined scatter image. This combining of the scatter images and this correction of the detection values based on the combined scatter image will be described in more detail further below.

The scatter contribution providing unit 11 is adapted to provide a scatter image set comprising scatter images being parameterized. For this parameterization functions are fitted to the scatter images, wherein the fitting parameters are stored and provided by the scatter contribution providing unit 11 instead of storing and providing complete scatter images. For example, Gaussian functions or polynomial functions can be fitted to the scatter images. For instance, the scatter image 15 shown in FIG. 2 can be parameterized by a Gaussian function, wherein the width and peak intensity are fitted to the scatter image. Thus, instead of storing and providing the complete scatter image 15 only the fitting parameters being the width and the peak intensity have to be stored and provided.

Figure 3:
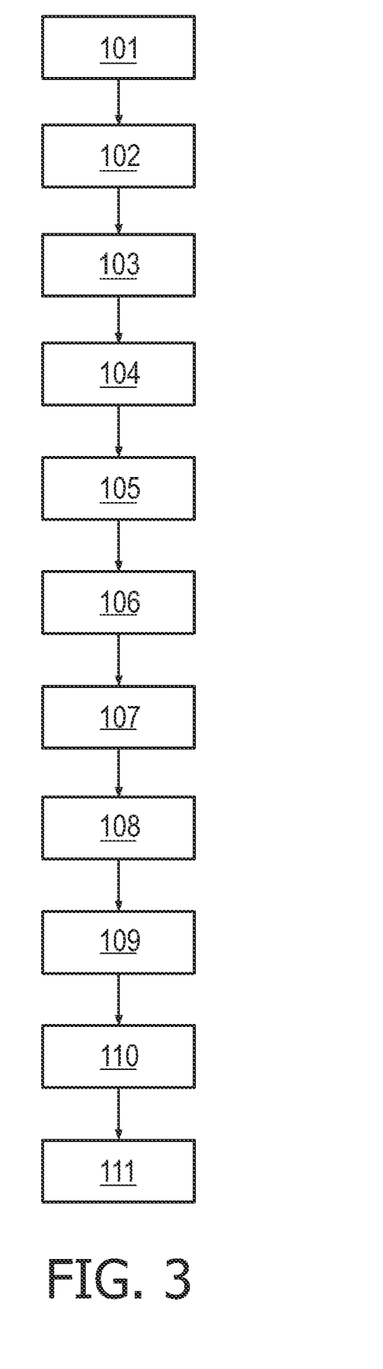
FIG. 3 shows exemplarily a flow chart illustrating a multi-energy computed tomography method and FIG. 4 shows exemplarily a flow chart illustrating a method for determining a scatter image.

In the following a multi-energy computed tomography method will be exemplarily described with reference to a flow chart shown in FIG. 3.

In step 101, the radiation source 2 rotates around the rotational axis A and the object or the examination zone 5 is not moved, i.e. the radiation source 2 travels along a circular trajectory around the object or the examination zone 5. In another embodiment, the radiation source 2 can move along another trajectory, for example, a helical trajectory, relative to the object. The radiation source 2 emits radiation traversing the object, wherein the radiation, which has traversed the object, is detected by the detection unit 6, which generates detection values being projection data. The projection data form several energy views, wherein an energy view is defined by a radiation source position with respect to the object and the same energy of the detection values of the energy view. The following steps 102 to 110 are performed for each energy view.

The detection values represent an intensity, an energy being, in this embodiment, an energy spectrum, a location on the detection surface and a radiation source position relative to the object, in particular, in this embodiment, the detection unit 6 comprises energy-windows, wherein each detection value depends on the intensity of the radiation in an energy-window of the detection unit for a certain position of the radiation source and a certain position on the two-dimensional detection surface of the detection unit.

In step 102, the correction unit 12 corrects the detection values of an energy view by normalizing the detection values with respect to air scan values which are preferentially measured in advance without an object present in the examination zone 5. Furthermore, in step 102 further correction procedures can be applied on the detection values, for example, a beam hardening correction can be applied on the detection values. This step 102 can be omitted in other embodiments or can be performed after step 110.

In step 103, a spatial down sampling is performed with the corrected detection values by the correction unit 12. The two-dimensional detection surface of the detection unit 6 comprises several detection elements which can be named pixels. The spatial down sampling reduces the number of pixels of the two-dimensional detection surface, i.e. reduces the number of detection values. This spatial down sampling is preferentially performed by averaging of detection values or by box-car filtering. Preferentially, the pixels are down-sampled by a factor of eight or more in each of the two dimensions of the detection surface. Also step 103 can be omitted.

In step 104, the correction unit 12 calculates for each detection value $P_E(i,j)$ of an energy view a water-equivalent thickness $T_E(i,j)$ according to following equation:

$$T_E(i,j)=[\ln P_E(i,j)]/\mu_E \quad (1)$$

The index E indicates the energy, i.e. the energy spectrum or energy distribution in this embodiment, of the respective energy view and the indices i,j indicate the position of the respective detection value of the energy view having the energy E on the two-dimensional detection surface. The variable $\mu_E$ denotes the mean attenuation coefficient of water for the respective energy, i.e. the radiation spectrum and energy window that have been used for generating the respective detection values.

The detection values have been normalized in step 102 such that a detection value $P_E(i,j)$ of 1 did not pass any object so that the corresponding ray did not contribute to a scatter. Without loss of generality, in the following such detection values can therefore be excluded and it can be assumed that the water-equivalent thickness is larger than zero.

In step 105, the gradient $\nabla T_E(i,j)$ is calculated, which for each coordinate (i,j) exhibits a certain value of magnitude $g_E(i,j)=|\nabla\nabla_E T(i,j)|$ and a direction angle $\phi_E(i,j)$.

The water-equivalent thickness and the gradient are preferentially determined, if the scatter images have been determined based on a model being a sphere. However, if the scatter images have been determined based on another model, other parameters might be extracted from the detection values, wherein these parameters can be used for selecting appropriate scatter images for a scatter correction. Another possibility is not to use an explicit physical model but to use a pre-defined empirical or semi-empirical mapping between the parameters extracted from the detection values or the detection values themselves and parameterized scatter images.

For each detection value having a water-equivalent thickness larger than zero, the obtained combination of water-equivalent thickness $T_E(i,j)$, gradient magnitude $g_E(i,j)$ and gradient direction $\phi_E(i,j)$ determines a uniquely defined sphere with radius $R_E(i,j)$ and offset vector $\vec{r}_E(i,j)=(r_E(i,j), \phi_E(i,j))$ in a plane parallel to the two-dimensional detector surface and relative to the respective detection values coordinates (i,j) as explained above and shown in FIG. 2. This sphere is defined in such a way that its parallel projection would at least substantially exhibit the same values of $T_E(i,j)$ and $g_E(i,j)$ at the respective detection value position (i,j) as the actual object. The respective mapping $[T_E(i,j), g_E(i,j)] \Rightarrow [R_E(i,j), r_E(i,j)]$ is performed in step 106 and is achieved by following equations:

$$R_E(i, j) = \frac{T_E(i, j)}{4}\sqrt{4 + g_E(i, j)^2} \quad (2)$$

and $$r_E(i, j) = \frac{T_E(i, j)}{4} g_E(i, j) \quad (3)$$

In flat image areas with negligible gradient, the positional offset $r_E(i,j)$ will be close to zero and $r_E(i,j)$ will approximately be given by $T_E(i,j)/2$. At steep gradients, $r_E(i,j)$ will be only slightly lower than $r_E(i,j)$, but since $T_E(i,j) \geq 0$, $r_E(i,j)$ always lies within the interval $[0, R)$. Instead of $(R,r,\phi)$, it is convenient to parameterize the utilized water sphere by $(R,\rho,\phi)$, where the offset ratio $\rho \epsilon [0,1)$ is defined as $\rho = r/R$.

The mapping performed in step 106 yields for each detection value $P_E(i,j)$ a scatter image $\kappa(R_E(i,j), \rho_E(i,j), \phi_E(i,j),i,j)$. The scatter image $\kappa(R_E(i,j), \rho_E(i,j), \phi_E(i,j),i,j)$ represents the scatter measured or simulated in an arrangement as exemplarily shown in FIG. 2, wherein a pencil beam is arranged perpendicular to the two-dimensional detection surface of the detection unit and meets the two-dimensional detection surface at the location indicated by the indices (i,j) and wherein the pencil beam traverses the model of the object being in this embodiment a sphere having the radius $R_E(i,j)$ with respect to the $\vec{r}_E(i,j)=(\rho_E(i,j), R_E(i,j), \phi_E(i,j))$ with respect to the isocenter.

If in another embodiment instead of a sphere another model of the object is used for determining the scatter images, wherein the scatter images are provided depending on certain scatter image parameters, detection value parameters are extracted from the detection values, and these extracted detection value parameters are mapped onto the scatter image parameters for selecting the scatter images used for correcting the respective detection values. In yet another embodiment no physical model is used, but an empirical or semi-empirical mapping between the parameters extracted from the detection values or the detection values themselves and parameterized scatter images is performed.

The scatter images form a scatter image set which is predetermined, wherein a scatter image is predetermined, for example, by simulating and/or measuring a scatter caused by radiation running along a path through a model of the object for at least one of a spectrum of radiation incident on the model of the object and an energy-window of the detection unit.

Figure 4:
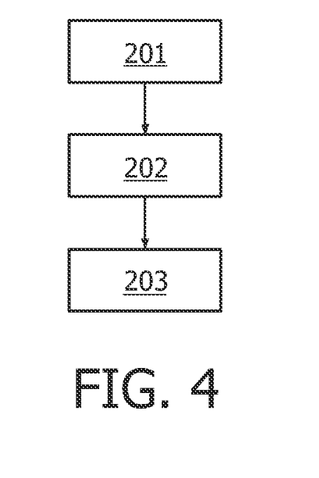

A method for determining a scatter image will in the following be exemplarily described with reference to a flow chart shown in FIG. 4.

For determining a scatter image $\kappa(R_E(i,j), \rho_E(i,j), \phi_E(i,j),i,j)$, in step 201 a model being in this embodiment a sphere having the radius $R_E(i,j)$ is centered at a position $\vec{r}_E(i,j)=(\rho_E(i,j), R_E(i,j), \phi_E(i,j))$ relative to the beam in a plane through the isocenter and parallel to the two-dimensional detection surface as schematically shown in FIG. 2 and described above with reference to this figure. This arrangement of the sphere in front of the two-dimensional detection surface can be performed by simulation or in reality.

In step 202, a pencil beam is directed to the detection element indicated by the indices (i,j), i.e. to the location on the two-dimensional detection surface indicated by (i,j). This pencil beam runs perpendicular to the two-dimensional detection surface as schematically and exemplarily shown in FIG. 2. Also this pencil beam can be a simulation or can be a real beam. Furthermore, in step 202 the image generated by the scatter, if this pencil beam traverses the model of the object, on the two-dimensional detection surface is detected as the scatter image. Also this detection can be performed in real or by simulations. The simulations are preferentially Monte-Carlo simulations. In Monte-Carlo simulations of an object, a large number of X-ray photons is tracked through the object, and for each X-ray photon interactions with the object, such as photoelectric absorption, elastic or inelastic scattering are taking place in a probabilistic manner. In such simulations, the energy dependent scattering probability of an X-ray photon in a material is specified by the scatter cross section of the material with respect to the different interactions, i.e. photoelectric absorption, elastic or inelastic scattering, and possibly further interaction mechanisms.

In step 203, the resulting scatter images are normalized to a pixel size of unit area and are divided by the respective values of primary radiation, thereby representing scatter-to-primary values.

These processed scatter images $\kappa(R_E(i,j), \rho_E(i,j), \phi_E(i,j),i,j)$ are used in the following for performing a scatter correction on the detection values $P_E(i,j)$. In particular, the scatter images $\kappa(R_E(i,j), \rho_E(i,j), \phi_E(i,j),i,j)$ can be used to express the contribution of a ray hitting the two-dimensional detection surface at coordinates (k,l) to the scatter signal at the location of another pixel (i,j) by $A \cdot P_E(k,l) \cdot \kappa(R_E(k,l), \rho_E(k,l), \phi_E(k,l), i-k,j-l)$. Thus, referring again to the flow chart shown in FIG. 3, in step 107 the combined scatter contribution to a detection value $P_E(i,j)$ is calculated according to following equation:

$$S_E(i, j) = w \cdot A \cdot \sum_{k,l} P_E(k, l) \cdot \kappa(R_E(k, l), \rho_E(k, l), \phi_E(k, l), i-k, j-l) \quad (4)$$

Here, w is a correction factor for a-posteriori optimization for adapting an iterative correction procedure which will be described further below. The correction factor w determines the degree of consideration of the scatter contribution in each iteration step. Preferentially, the correction factor w is one or close to one, for example, 0.95. Furthermore, A denotes the area of a detection element, i.e. of a pixel, of the two-dimensional detection surface.

Equation (4) describes a combination of scatter contributions, in particular, of scatter images, performed by the scatter contributions combining unit 30.

Equation (4) describes a convolution-like procedure, wherein the scatter images $\kappa(R_E(k,l), \rho_E(k,l), \phi_E(k,l),i-k,j-l)$ can be regarded as a kernel and wherein the scatter contribution $S_E(i,j)$ is determined by the convolution-like procedure using the detection values $P_E(i,j)$ and the kernel $\kappa(R_E(k,l), \rho_E(k,l), \phi_E(k,l),i-k,j-l)$.

In step 108, the detection values are corrected based on the combined scatter contribution $S_E(i,j)$ determined in step 107. Correction might either be performed in a subtractive or in a multiplicative way.

The subtractive correction can be performed according to following equation:

$$I_E^{(\nu+1)}(i,j)=I_E^{(0)}(i,j)-S_E^{(\nu)}(i,j). \quad (5)$$

The upper indices indicate that the correction is preferentially performed iteratively, wherein $I_E^{(\nu)}(i,j)$ denotes the corrected detection values after $\nu$ iterations. Thus, $I_E^{(0)}(i,j)$ denotes the detection values before the scatter correction, and $S_E^{(\nu)}(i,j)$ denotes the respective combined scatter contribution, which has been calculated by using the corrected detection values $I_E^{(\nu)}(i,j)$ and which can be defined by following equation:

$$S_E^{(v)}(i, j) = \qquad (6)$$
$$w \cdot A \cdot \sum_{k,l} I_E^{(v)}(k, l) \cdot \kappa(R_E^{(v)}(k, l), \rho_E^{(v)}(k, l), \phi_E^{(v)}(k, l), i-k, j-l)$$

It should be noted that while performing the iterative correction in accordance with equations (5) and (6), for each iteration step the scatter images $\kappa(R_E^{(v)}(k,l), \rho_E^{(v)}(k,l), \phi_E^{(v)}(k,l), i-k, j-l)$ that correspond to the actually corrected detection values $I_E^{(v)}(i,j)$ are used, i.e. wherein $$R_E^{(v)}(k, l) = \frac{T_E^{(v)}(k, l)}{4} \sqrt{4 + g_E^{(v)}(k, l)^2}, \qquad (7)$$

$$\rho_E^{(v)}(k, l) = \frac{T_E^{(v)}(k, l)}{4 R_E^{(v)}(k, l)} g_E^{(v)}(k, l), \qquad (8)$$

$$g_E^{(v)}(k, l) = |\nabla T_E^{(v)}(k, l)| \qquad (9)$$
and
$$T_E^{(v)}(k, l) = -[\ln I_E^{(v)}(k, l)]/\mu, \qquad (10)$$

wherein $\phi_E^{(v)}(k,l)$ denotes the angular direction of the gradient $\nabla T_E^{(v)}$.

For performing a multiplicative correction instead of equation (5) following equation is used:

$$I_E^{(v+1)}(i, j) = \frac{I_E^{(0)}(i, j) \cdot I_E^{(v)}(i, j)}{I_E^{(v)}(i, j) + S_E^{(v)}(i, j)}. \qquad (11)$$

The iteration is performed until a stopping criterion is fulfilled. Preferentially, consecutive views $I_E^{(v)}(i,j)$ and $I_E^{(v+1)}(i,j)$ are compared. If a similarity measure applied to these two consecutive images yields a similarity value larger than a predefined threshold, the iteration is stopped. The similarity measure is, for example, the inverse of squared differences of corresponding detection values of the two consecutive images.

In step 109, the resulting combined scatter contribution $S_E^{(v)}(i,j)$ is up-sampled to the number of originally acquired detection values of a view, i.e. to the number of detection elements of the detection unit 6. If, in another embodiment, the down-sampling step 103 is omitted, also the up-sampling 109 is omitted.

In step 110, the determined combined scatter contribution $S_E^{(v)}(i,j)$ is subtracted from the detection values which have been corrected in step 102. If the correction step 102 is not performed, the combined scatter contribution $S_E^{(v)}(i,j)$ is subtracted from the originally acquired detection values.

Steps 102 to 110 can be regarded as the steps of a detection values correction method.

In step 111, the reconstruction unit 13 reconstructs an image of the object by using the corrected energy views. For example, for each energy an image is reconstructed using the respective energy views. The reconstruction is preferentially performed by backprojection. However, instead of backprojection another reconstruction procedure can be used like Radon inversion.

In the above described embodiment, the model is a sphere, in other embodiments, other models can be used instead of a sphere, for example, a water-slab model or an elliptical model.

Although in the above described embodiments the multi-energy imaging system is a multi-energy computed tomography system, in other embodiments, another imaging system can be used as multi-energy imaging system, for example, another imaging system that generates and/or uses multi-energy projection images like an X-ray C-arm system.

Although in the above described embodiments a combined scatter contribution has been determined using a certain convolution-like error correction which has been described above with reference to equations (4) and (6), in other embodiments other convolution-like error correction procedures can be used for performing a scatter correction on the detection values by using scatter kernels, wherein the used scatter kernels represent scatter contributions as defined in claim 1.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or devices may fulfill the functions of several items recited in the claims. The mere fact that certain measures are recited in mutually different dependent claims does not indicate that a combination of these measures cannot be used to advantage. For example, the parameterized scatter images of claim 5 are preferentially based on scatter images measured and/or simulated in accordance with claim 3 or 4.

Calculations like the determination of scatter contributions, in particular, of scatter images, or the correction of the detection values by using the scatter contributions, in particular, the scatter images, or the reconstruction performed by one or several units or devices can be performed by any other number of units or devices. For example, steps 102 to 111 can be performed by a single unit or by any other number of different units. Also steps 201 to 203, in combination with steps 102 to 111 or not in combination with steps 102 to 111, can be performed by a single unit or device or by any other number of different units or devices. The calculations and determinations and/or the control of the detection values correction apparatus in accordance with the above described correction of detection values and/or the control of the scatter contribution providing unit in accordance with the above described provision of the scatter contributions and/or the control of the multi-energy computed tomography system in accordance with the above described multi-energy computed tomography method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A detection values correction apparatus that corrects detection values of a projection image of a multi-energy imaging system comprising a radiation source for emitting radiation for traversing an object and a detection unit having different energy-windows and comprising a detection surface for generating the detection values depending on the radiation after having traversed the object, wherein a detection value represents an intensity, an energy and a location on the detection surface, wherein the detection values correction apparatus comprises:
- a scatter contribution providing unit that provides scatter contributions produced by radiation running along paths through the object for the different energy-windows of the detection unit for different intensities, different energies and different locations on the detection surface of the detection values, wherein a scatter contribution represents the contribution of the scatter, which is generated by radiation of a detection value representing an intensity, an energy and a location on the detection surface, to the detection value to be corrected,
- a scatter contributions combining unit that combines scatter contributions for correcting a detection value, wherein the combined scatter contributions represent the contribution of the scatter, which is caused by radiation of the other detection values of the projection image, to the detection value to be corrected and wherein the scatter contributions are combined under consideration of the intensity, energy and location on the detection surface of the other detection values, and
- a correction unit that scatter corrects the detection value of the projection image by using the combined scatter contributions.

2. The detection values correction apparatus as defined in claim 1, I wherein the scatter contribution providing unit provides scatter images, wherein each scatter image represents scatter contributions to the detection values of the projection image generated by radiation of a detection value representing an intensity, an energy and a location on the detection surface.

3. The detection values correction apparatus as defined in claim 2, wherein the scatter contributions providing unit provides a scatter image by simulating and/or measuring a scatter generated by radiation along a path to a detection value representing an intensity, an energy and a location on the detection surface through a model of the object.

4. The detection values correction apparatus as defined in claim 3, wherein the model of the object is a model representing at least one of a) multiple materials and b) an average material comprising a scatter characteristic being an average of scatter characteristics of multiple materials.

5. The detection values correction apparatus as defined in claim 2, I wherein the scatter contribution providing unit provides scatter images being parameterized.

6. A scatter contribution providing unit that provides scatter contributions being usable with a detection values correction apparatus for correcting detection values of a projection image of a multi-energy imaging system comprising a radiation source that emits radiation for traversing an object and a detection unit having different energy-windows and comprising a detection surface that generates the detection values depending on the radiation after having traversed the object, wherein a detection value represents an intensity, an energy and a location on the detection surface, wherein the scatter contribution providing unit provides scatter contributions produced by radiation running along paths through the object for the different energy-windows of the detection unit for different intensities, different energies and different locations on the detection surface of the detection values, wherein a scatter contribution represents the contribution of the scatter, which is generated by radiation of a detection value representing an intensity, an energy and a location on the detection surface, to the detection value to be corrected.

7. A multi-energy imaging system comprising:
- a radiation source that emits radiation for traversing an object,
- a detection unit comprising multiple different energy-windows and a detection surface that generates detection values of a projection image depending on the radiation after having traversed the object, wherein a detection value represents an intensity, an energy and a location on the detection surface,
- a detection correction apparatus that corrects detection values of a projection image of the multi-energy imaging system, the detection values correction apparatus comprising:
  - a scatter contribution providing unit that provides scatter contributions produced by radiation running along paths through the object for the different energy-windows of the detection unit for different intensities, different energies and different locations on the detection surface of the detection values, wherein a scatter contribution represents the contribution of the scatter, which is generated by radiation of a detection value representing an intensity, an energy and a location on the detection surface, to the detection value to be corrected,
  - a scatter contributions combining unit that combines scatter contributions for correcting a detection value, wherein the combined scatter contributions represent the contribution of the scatter, which is caused by radiation of the other detection values of the projection image, to the detection value to be corrected and wherein the scatter contributions are combined under consideration of the intensity, energy and location on the detection surface of the other detection values, and
  - a correction unit that scatter corrects the detection value of the projection image by using the combined scatter contributions.

8. The multi-energy imaging system as defined in claim 7, wherein the radiation source and the detection unit acquire detection values representing predefined energies, wherein the scatter contribution providing unit stores predetermined scatter contributions for different intensities, the predefined energies and different locations on the detection surface of the detection values.

9. The multi-energy imaging system as defined in claim 7, wherein the radiation source and the detection unit acquire detection values representing predefined energies, wherein the scatter contribution providing unit provides the scatter contributions by combining predetermined scatter contributions, which have been predetermined for different intensities, different energies and different locations on the detection surface, such that the resulting scatter contributions represent the contribution of the scatter, which is caused by radiation of detection values representing different intensities, the predefined energies and different locations on the detection surface, to a detection value to be corrected.

10. A detection values correction method for correcting detection values of a projection image of a multi-energy imaging system comprising a radiation source that emits radiation for traversing an object and a detection unit having different energy-windows and comprising a detection surface that generates the detection values depending on the radiation after having traversed the object, wherein a detection value represents an intensity, an energy and a location on the detection surface, wherein the detection values correction method comprises following steps:
- providing scatter contributions produced by radiation running along paths through the object for the different energy-windows of the detection unit for different intensities, different energies and different locations on the detection surface of the detection values, wherein a scatter contribution represents the contribution of the scatter, which is generated by radiation of a detection value representing an intensity, an energy and a location on the detection surface, to the detection value to be corrected, combining scatter contributions for correcting a detection value, wherein the combined scatter contributions represent the contribution of the scatter, which is caused by radiation of the other detection values of the projection image, to the detection value to be corrected and wherein the scatter contributions are combined under consideration of the intensity, energy and location on the detection surface of the other detection values, scatter correcting the detection value of the projection image by using the combined scatter contributions.

11. A scatter contribution providing method for providing scatter contributions being usable with a detection values correction method for correcting detection values of a projection image of a multi-energy imaging system comprising a radiation source for emitting radiation for traversing an object and a detection unit having different energy-windows and comprising a detection surface for generating the detection values depending on the radiation after having traversed the object, wherein a detection value represents an intensity, an energy and a location on the detection surface, wherein scatter contributions are produced by radiation running along paths through the object for the different energy-windows of the detection unit for different intensities, different energies and different locations on the detection surface of the detection values are provided, wherein a scatter contribution represents the contribution of the scatter, which is caused by radiation of a detection value representing an intensity, an energy and a location on the detection surface, to the detection value to be corrected.

12. A multi-energy imaging method comprising:
emitting radiation for traversing an object by a radiation source,
generating detection values of a projection image depending on the radiation after having traversed the object, wherein a detection value represents an intensity, an energy and a location on the detection surface, by a detection unit comprising a detection surface,
correcting the detection values of the projection image by the detection values correction method as defined in claim 10.

13. The scatter contribution providing unit as defined in claim 6, wherein the scatter contribution providing unit provides scatter images, wherein each scatter image represents scatter contributions to the detection values of the projection image generated by radiation of a detection value representing an intensity, an energy and a location on the detection surface.

14. The scatter contribution providing unit as defined in claim 13, wherein the scatter contributions providing unit provides a scatter image by simulating and/or measuring a scatter generated by radiation along a path to a detection value representing an intensity, an energy and a location on the detection surface through a model of the object.

15. The scatter contribution providing unit as defined in claim 14, wherein the model of the object is a model representing at least one of a) multiple materials and b) an average material comprising a scatter characteristic being an average of scatter characteristics of multiple materials.

16. The scatter contribution providing unit as defined in claim 15, wherein the scatter contribution providing unit provides scatter images being parameterized.

17. The method as defined in claim 10, wherein providing scatter contributions includes providing scatter images, wherein each scatter image represents scatter contributions to the detection values of the projection image generated by radiation of a detection value representing an intensity, an energy and a location on the detection surface.

18. The method as defined in claim 17, where providing a scatter image includes simulating and/or measuring a scatter generated by radiation along a path to a detection value representing an intensity, an energy and a location on the detection surface through a model of the object.

19. The method as defined in claim 18, wherein the model of the object is a model representing at least one of a) multiple materials and b) an average material comprising a scatter characteristic being an average of scatter characteristics of multiple materials.

20. The method as defined in claim 19, wherein providing scatter contributions includes providing scatter images that are parameterized.

* * * * *